US006465498B2

(12) United States Patent
Beilfuss et al.

(10) Patent No.: US 6,465,498 B2
(45) Date of Patent: *Oct. 15, 2002

(54) USE OF DERIVATIVES OF METHYLENE-BIS-OXAZOLIDINE AND COMPOSITIONS OBTAINED THEREBY

(75) Inventors: Wolfgang Beilfuss, Hamburg; Ralf Gradtke, Tornsch, both of (DE)

(73) Assignee: Air Liquide Sante (International), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/986,938

(22) Filed: Nov. 13, 2001

(65) Prior Publication Data

US 2002/0058684 A1 May 16, 2002

Related U.S. Application Data

(62) Division of application No. 09/391,649, filed on Sep. 8, 1999, now Pat. No. 6,348,483.

(30) Foreign Application Priority Data

Sep. 7, 1998 (DE) .......................................... 198 42 116

(51) Int. Cl.⁷ ............................................... A01N 43/76
(52) U.S. Cl. ........................................................ 514/374
(58) Field of Search ........................................... 514/374

(56) References Cited

U.S. PATENT DOCUMENTS

| 3,939,272 A | | 2/1976 | McCoy et al. |
| 4,166,122 A | | 8/1979 | Paulus et al. |
| 4,148,905 A | * | 4/1997 | Eggensperger et al. ..... 424/405 |

FOREIGN PATENT DOCUMENTS

| DE | 2635389 | | 2/1978 |
| EP | 522393 | | 1/1993 |
| EP | 601674 | | 6/1994 |
| FR | 2405018 | | 5/1979 |
| JP | 49093537 | * | 9/1974 |
| JP | 622260002 | | 11/1986 |
| JP | 62099309 | | 5/1987 |

* cited by examiner

Primary Examiner—Alton Pryor
(74) Attorney, Agent, or Firm—Young & Thompson

(57) ABSTRACT

The present invention relates to stable microbicidal compositions which are characterized in that they comprise derivatives of methylenebisoxazolidine and 1H-benzimidazol-2-ylcarbamic acid. The compositions according to the invention can be employed in industrial products. The derivatives of methylenebisoxazolidine are used, in particular, for increasing the solubility of derivatives of 1H-benzimidazol-2-ylcarbamic acid in liquid preparations.

25 Claims, No Drawings

USE OF DERIVATIVES OF METHYLENE-BIS-OXAZOLIDINE AND COMPOSITIONS OBTAINED THEREBY

This application is a division of Ser. No. 09/391,649 filed Sep. 8, 1999 now U.S. Pat. No. 6,348,483.

FIELD OF THE INVENTION

The present invention relates to the use of methylenebisoxazolidine derivatives for increasing the solubility of derivatives of 1H-benzimidazol-2-ylcarbamic acid in liquid preparations or preservatives for use in industrial products.

Methyl 1H-benzimidazol-2-ylcarbamate (carbendazim) is known in the prior art as a fungicide. The active compound has no bactericidal action and is virtually insoluble in water and in most organic solvents. Thus, only via salt formation, for example using strong acids such as HCl, $H_2SO_4$, Malon AS 3 acid (4-$C_{10-13}$-sec-alkyl derivative of benzenesulphonic acid), is it possible to improve the solubility of carbendazim in preparations to such an extent that use in liquid concentrates, for example, is possible. However, in some cases salt formation requires a considerable reaction expense. Thus, for example for preparing carbendasulf (salt of carbendazim and mono-$C_{10-14}$-alkylbenzenesulphonic acid) requires heating carbendazim with Malon AS 3 acid in propylene glycol for 4 hours. Moreover, by-products are formed in this reaction, resulting in losses of activity. Although the concentration of carbendazim in the liquid concentrates described is below 4% by weight, precipitation frequently occurs after some time. Carbendazim and carbendasulf are virtually insoluble in aqueous systems.

Aqueous dispersions based on carbendazim, such as the commercial product Parmetol DF 19 Forte (aqueous dispersion based on carbendazim (fungicide) and diuron (1,1-dimethyl-3-(3,4-dichlorophenyl)urea) (algicide)) are known. However, such preparations are not water-soluble. Stable carbendasulf-comprising concentrates having a limited content of carbendasulf (for example the commercial product Parmetol DF 18) are likewise known from the prior art. However, they have an unsatifactory stability towards low temperatures, and they do not form any clear solutions in water.

Hitherto, the preparation of an aqueous preparation comprising carbendazim or carbendasulf as fungicidal active compound did not seem to be possible or economical.

Derivatives of methylenebisoxazolidine, such as 3,3'-methylenebis-(5-methyloxazolidine) (trade name: Mar 71) are used as water-soluble bactericides; however, in practice they frequently only have low fungicidal activity.

Liquid preparations of Mar 71 and the fungicide Kathon 893 (preparation of N-octylisothiazolone in 1,2-propylene glycol), for example, are known. However, these products are not sufficiently stable towards alkali, and in particular the fungicide decomposes at a pH above about 9.5 and is furthermore subject to degradation by nucleophilic agents.

OBJECT OF THE INVENTION

It was therefore an object of the present invention to increase the solubility of derivatives of 1H-benzimidazol-2-ylcarbamic acid in liquid preparations and to provide compositions which, in addition to good fungicidal or algicidal activity, also have satisfactory bactericidal and, if appropriate, virucidal activity. With a view to possible applications in cooling lubricants (concentrates and emulsions), in the fungicidal, algicidal, bactericidal and/or virucidal finishing of products or coatings such as paints, renders and sealing materials, the substances used should have satisfactory stability towards alkali.

SUMMARY OF THE INVENTION

This object is achieved by using derivatives of methylenebisoxazolidine to increase the solubility of derivatives of 1H-benzimidazol-2-ylcarbamic acid in liquid preparations.

The invention accordingly also provides stable microbicidal compositions which are characterized in that they comprise derivatives of methylenebisoxazolidine and 1H-benzimidazol-2-ylcarbamic acid. Here, microbicidal compositions are to be understood as meaning algicidal, bactericidal, fungicidal and/or virucidal compositions.

The present invention furthermore provides the use of such compositions.

Preferred embodiments are the subject of the subclaims.

Surprisingly, it has been found that homogeneous clear solutions of derivatives of 1H-benzimidazol-2-ylcarbamic acid (carbendazim) can be prepared in the presence of derivatives of methylenebisoxazolidine.

Furthermore, it has been found that by using derivatives of methylenebisoxazolidine and, if appropriate, other active compounds, additives and/or auxiliaries, it is possible to obtain clear homogeneous concentrates whose content of carbendazim can be above 10% by weight.

These concentrates can be employed to prepare, by dilution with water, ready-to-use solutions which are likewise clear and homogeneous. In addition to good bactericidal action, these ready-to-use dilutions have excellent fungicidal and algicidal action and/or virucidal activity.

Advantageously, the odour and the emission of formaldehyde of the resulting preparations are simultaneously, in particular at high contents of carbendazim, strongly reduced.

The preparations furthermore have, by comparison, excellent stability towards alkali and low temperatures. Moreover, they have a sufficiently high buffer capacity to maintain an alkaline medium.

The emission of formaldehyde or formaldehyde depot compounds from these preparations according to the invention is considerably lower than that of the preparations based on the individual components, for example Mar 71. Furthermore, the use according to the invention of methylenebisoxazolidine together with carbendazim results in synergistic action.

The compositions according to the invention generally have a pH of up to 12, in particular up to 11 and preferably up to 10.

For preparing the compositions according to the invention, use is preferably made of 3,3'-methylenebis-(5-methyloxazolidine) (trade name Mar 71).

Preferred carbamic acid derivatives are selected from methyl 1H-benzimidazol-2-ylcarbamate or its salts, for example the monohydrochloride, the monohydrobromide or the salt of Malon AS 3 acid, and methyl 1-(butylcarbamoyl) benzimidazol-2-ylcarbamate.

The compositions may comprise further active compounds, in particular N-formals and/or O-formals, additives and/or auxiliaries. It is possible to add, for example, the following substances:

further microbicidally active compounds, such as
N-formals (for example Grotan BK, alpha, alpha', alpha"-trimethyl-1,3,5-triazine-1,3,5-(2H,4H,6H)-triethanol, 4,4-dimethyloxazolidine, dimethylolurea, 5-ethyl-3,7-dioxa-1-azabicyclo [3.3.0] octane, 2-(hydroxymethylamino) ethanol, methylenebistetrahydro-1,3-bisoxazine, N-methylolchloroacetamide, bis(hydroxymethyl)-5,5-dimethylhydantoin, diazolidinylurea, Na-hydroxymethylglycinate, 3,4,4-trimethyloxazolidine), O-formals (for example propylene glycol hemiformal, propylene glycol bishemiformal, ethylene glycol bishemiformal, benzyl alcohol hemiformal, butyl diglycol hemiformal), heterocycles (for example 1,2-benzisothiazolin-3-one, 5-chloro-2-methylisothiazolin-3-one, 2-methylisothiazolin-3-one, N-octylisothiazolin-3-one, 2-mercaptopyridine N-oxide or its salts, such as Na or zinc salt, pyrion disulphide, thiabenzazole, N-cyclohexylbenzo(b)thiophene-2-carboxamide 1,1-dioxide), halogenated organic compounds (for example 3-iodopropinyl butylcarbamate, 2-bromo-2-nitropropane-1,3-diol, dibromodicyanobutane)

other active compounds, such as N-cyclohexyl-N-nitrosohydroxylamine or its salts, such as Na, K or Al salts algicides, such as diuron (1,1-dimethyl-3-(3,4-dichlorophenyl)urea), Irgarol 1051 (2-methylthio-4-tert-butylamino-6-cyclopropylamino-s-triazine), terbutryn (2-methylthio-4-tert-butylamino-6-ethylamino-s-triazine)

insecticides, acaricides, nematocides substances for regulating or adjusting the pH (for example amines or alkanolamines, in particular primary and tertiary amines or alkanolamines, acids, carboxylic acids, salts, buffers)

odour-masking substances, odour modifiers, perfume colorants additives for protection against corrosion stabilizers solvents, such as water, alcohols, glycols, glycol ethers, etc. (for example ethanol, propanols, 1,2-propylene glycol, triethylene glycol, 1-methoxypropan-2-ol, butyl diglycol, phenoxyethanol, phenoxypropanols)

The compositions according to the invention can comprise aqueous and/or organic phases. They can be present in liquid, liquid-viscous or paste-like form. They can be present in the form of a concentrate or a ready-to-use solution.

The content of carbamic acid derivative(s) is generally greater than 1% by weight, preferably greater than 5% by weight and in particular greater than 10% by weight.

The content of methylenebisoxazolidine derivative(s) is generally not greater than 99% by weight, preferably not greater than 95% by weight and in particular not greater than 90% by weight.

The compositions according to the invention may also comprise only carbamic acid derivative(s) and methylenebisoxazolidine derivative(s), without other substances being added.

The compositions according to the invention are generally prepared by methods known in the art. In general, it is sufficient to simply mix the components at room temperature or with heating, for example to up to 100° C., in combination with work-up steps such as filtration and the like, to obtain the compositions according to the invention.

The preparations obtained according to the invention can be incorporated advantageously into industrial products, such as liquid microbicidal products and water-soluble microbicidal products, and be used in crop protection or in the treatment of seed (plant hygiene). Furthermore, they can be incorporated into industrial preservatives having microbicidal activity, container preservatives, cutting fluid additives, fuel additives and other industrial preservatives. They can also be employed in disinfectants, in particular in low-foam disinfectants having microbicidal activity. They can also be used in compositions for controlling pruning wound parasites on plants, compositions for treating plant pruning wounds, disinfectants for applications where colonization by fungi is very likely, film preservatives for external and in particular internal applications and wood protection compositions.

The incorporation of the compositions according to the invention into industrial products, for example those mentioned above, can be carried out by adding the previously finished composition. Alternatively, the addition can be carried out by incorporating the components of the compositions according to the invention separately at the same time, or else at different times, into the industrial products.

The concentrations used here are generally greater than 0.01% by weight, preferably greater than 0.05% by weight and in particular greater than 0.10% by weight, based on the weight of the industrial product.

DETAILED DESCRIPTION OF THE INVENTION

EXAMPLES

Example 1

Preparations Based on Fungicides or Biocides and Specific N-formals

TABLE 1

Test materials and test methods

| | |
|---|---|
| Fungi-algae test: | |
| Test material | Pure acrylate house paint |
| Test method | Fungicidal finish (SM 022) |
| | Algistatic finish (SM 023) |
| Test germs algae | *Chlorella fusca* (CF) |
| Test germs fungi | *Aspergillus niger* (AN) |
| | *Penicillium funiculosum* (PF) |
| | *Alternaria alternata* (AL) |
| Test substances: | |
| Blank | House paint without preservative |
| DF 27 | Parmetol DF 27* (as standard) |
| 431/043 | 90% by weight of Mar 71 + 10% by weight of carbendazim |
| Mar 71 | 3,3'-Methylenebis(5-methyloxazolidine) |
| 426/160 | 9% by weight of carbendazim dispersion (content of active compound based on the dispersion) |

*Parmetol DF 27 = aqueous dispersion of Irgarol 1051 (2-methylthio-4-tert-butylamino-6-cyclopropylamino-s-triazine), carbendazim and zinc pyrithion Procedure:

In separate batches, the test concentrations of the active compounds/products were incorporated into the house paint, and the fungicidal and/or algistatic finish was determined using the stated test methods. Incorporation and testing were carried out according to the methods SM 022 and SM 023 below.

Test Method SM-022

Determination of the Resistance to Fungal Attack

This laboratory method was used to determine the resistance of house coatings to fungal attack. For the method, house coatings on standardized paper were used as test substrate, and Aspergillus niger (ATCC 6275) and Penicillium funiculosum (ATCC 36839) were used as test fungi. The experiments were carried out in Petri dishes on dextrose nutrient medium.

Sample Preparation:

50 g of the material to be finished were, in separate batches, mixed with various concentrations of the fungicide to be examined and homogenized for 3–5 min using a basket stirrer.

Preparation of the Test Objects:

Paper carrier materials having the dimensions 90×270 mm (Schleicher & Schüll No. 2589 B/X 24078) were coated with the test material. The paint and/or render samples were coated to a wet-layer thickness of 250 $\mu$m by knife coating. The knife had an opening of a width of at least 6.5 cm. In the case of renders, the layer thickness depended, as in practice, on the particle size. The coated carrier materials, hereinbelow referred to as test bodies, were subsequently dried in a horizontal position for five days.

Pretreatment of the Test Bodies:

The test bodies were watered in running tap water of 15±5° C. and a flow rate of 1 l/min for 72 hours and subsequently dried for two days. The cross section of the container for the watering in the direction of flow was 1000±500 cm$^2$.

From the pretreated test bodies, sample bodies having a diameter of 5 cm were punched out and sterilized in a Co$^{60}$ source using at least 10 kGy.

Test Protocol:

Inoculation and Incubation:

The Sabouraud dextrose agar, which had solidified in the Petri dish, was inoculated with 0.2 ml of spore suspension (10$^7$ spores/ml) and plated out using a sterile Drigalski spatula or an offset sterile glass rod.

The pretreated sample bodies were then evenly placed onto the inoculated surface of the nutrient medium using a pair of tweezers, making sure that the entire surface of the sample body was in contact with the surface of the nutrient medium. The sample was subsequently incubated at 30±2° C. for three weeks. For other test germs, the incubation temperature had to be adapted to achieve optimum growth.

Evaluation:

After one, two and three weeks, the sample bodies were examined for fungal growth. Evaluation was carried out visually or—if this was required to exclude foreign infections—using a magnifying glass. If the extent of the colonization by foreign organisms observed considerably interfered with the evaluation, the experiment could not be evaluated and was repeated. The evaluation of the samples was based on the following evaluation scale:

00—entire plate free from colonization*
0—zone formation (no colonization around the sample)*
(0)—fungal colonization up to the sample*
1—only the sample edge is colonized*
2—the sample is colonized from the edge inwards (less than 25%)
3—the sample surface is colonized by individual colonies (25–75%)
4—the sample surface is colonized extensively (75% and more, but not the entire surface)
5—the sample surface is colonized completely (100%)
*Note: Samples evaluated as 00, 0, (0) and 1 can be referred to as "being effectively finished against fungal growth".

Test Method SM-023

Determination of the Resistance to Colonization by Algae

This laboratory method was employed for determining the resistance of house coatings to colonization by algae. For this method, house coatings on standardized paper are used as test substrate and Chlorella fusca is used as test alga. It is furthermore possible to use pure cultures of other algae species of practical relevance.

The experiments were carried out in Petri dishes on agar nutrient media.

Sample Preparation:

50 g of the material to be finished were, in separate batches, mixed with various concentrations of the algicide to be examined and homogenized for 3–5 min using a basket stirrer.

Preparation of the Test Objects:

Paper carrier materials having the dimensions 90×270 mm (Schleicher & Schüll No. 2589 B/X 24078) were coated with the test material. The paint and/or render samples were coated to a wet-layer thickness of 250 $\mu$m by knife coating. The knife had an opening of a width of at least 6.5 cm. In the case of renders, the layer thickness depends, as in practice, on the particle size. The coated carrier materials, hereinbelow referred to as test bodies, were subsequently dried in a horizontal position for five days.

Pretreatment of the Test Bodies:

The test bodies were watered in running tap water of 15±5° C. and a flow rate of 1 l/min for 72 hours and subsequently dried for two days. The cross section of the container for the watering in the direction of flow was 1000±500 cm$^2$.

From the pretreated test bodies, three sample bodies having a diameter of 5 cm were punched out and sterilized in a Co$^{60}$ source using at least 10 kGy.

Test Protocol:

Inoculation and Incubation:

Aseptically, the samples were placed onto the algae nutrient media, and the centre of the sample was inoculated with 5 ml of each algae suspension.

The mixture of the algae suspensions was spread on the surface using a Drigalski spatula or an offset sterile glass rod.

During the growth phase at 22±20° C., the coated samples in the Petri dishes were irradiated with light of an intensity of about 1000 Lux (customary fluorescent tubes, type D 67 daylight). A cycle of in each case 12 hours of irradiation and 12 hours of storage in the dark was used.

Evaluation:

The colonization of the samples by algae was examined and evaluated after two weeks. Evaluation was carried out visually. The evaluation of the samples was based on the following evaluation scale:

Group 1:

No growth of algae on the test bodies

Formation of an inhibitory zone or growth of algae on the nutrient medium up to the edge of the test bodies Paints of this group can be characterized by the term "effectively finished against colonization by algae".

Group 2:

Visible colonization of the test body by algae

| | | |
|---|---|---|
| − | = | no growth |
| + | = | some growth |
| ++ | = | moderate growth |
| +++ | = | strong growth |

The results are shown in Tables 2 and 3 below.

TABLE 2

Results of the tests from Table 1 on the algicidal activity

| Test substances: | Use concentration | Inhibitory zone in mm | Surface colonization | Remarks |
|---|---|---|---|---|
| Algistatic finish: without stress due to leaching | | | | |
| Blank | | 0 | +++ | None |
| Parmetol DF 27 | 3.0% by weight | >18 | − | Without discoloration |
| | 2.0% by weight | >18 | − | Without discoloration |
| | 1.0% by weight | >18 | − | Without discoloration |
| 431/043 | 2.0% by weight | >18 | − | Without discoloration |
| | 1.0% by weight | >18 | − | Without discoloration |
| | 0.5% by weight | >18 | − | Without discoloration |
| Mar 71 | 2.0% by weight | >18 | − | Without discoloration* |
| | 1.0% by weight | >18 | − | Without discoloration |
| | 0.5% by weight | 12 | − | Without discoloration |
| 426/160 | 2.22% by weight | 0 | +++ | Without discoloration |
| | 1.11% by weight | 0 | +++ | Without discoloration |
| | 0.55% by weight | 0 | +++ | Without discoloration |
| Algistatic finish: stress due to 72 hours leaching | | | | |
| Blank | | 0 | +++ | None |
| Parmetol DF 27 | 3.0% by weight | >18 | − | Without discoloration |
| | 2.0% by weight | >18 | − | Without discoloration |
| | 1.0% by weight | >18 | − | Without discoloration |
| 431/043 | 2.0% by weight | 0 | ++ | Without discoloration |
| | 1.0% by weight | 0 | ++ | Without discoloration |
| | 0.5% by weight | 0 | ++ | Without discoloration |
| Mar 71 | 2.0% by weight | 0 | +++ | Without discoloration |
| | 1.0% by weight | 0 | ++ | Without discoloration* |
| | 0.5% by weight | 0 | ++ | Without discoloration |
| 426/160 | 2.22% by weight | 0 | +++ | Without discoloration |
| | 1.11% by weight | 0 | +++ | Without discoloration |
| | 0.55% by weight | 0 | +++ | Without discoloration |

Key:
*Some lumps are formed in the house paint
− = no growth
+ = some growth
++ = moderate growth
+++ = strong growth

TABLE 3

Results of the tests from Table 1 on the fungicidal activity

| Fungicidal finish: | Use conc. | AN | | PF | |
|---|---|---|---|---|---|
| | | \multicolumn{4}{c}{Test germs} | | | |

| Fungicidal finish: | Use conc. | AN | | PF | |
|---|---|---|---|---|---|
| Without stress due to leaching | | | | | |
| Time (weeks) | | 1 | 2 | 1 | 2 |
| Blank | | 5 | 5 | 5 | 5 |
| Parmetol DF 27 | 3.0% by weight | 0 | 0 | 0 | 0 |
| | 2.0% by weight | 0 | 0 | 0 | 0 |
| | 1.0% by weight | 0 | (0) | 0 | 0 |
| 431/043 | 2.0% by weight | 0 | 1 | 00 | 00 |
| | 1.0% by weight | 1 | 2 | 0 | 0 |
| | 0.5% by weight | 1 | 2 | 0 | 0 |
| Mar 71 | 2.0% by weight | 5 | 5 | 3 | 4 |
| | 1.0% by weight | 5 | 5 | 5 | 5 |
| | 0.5% by weight | 5 | 5 | 5 | 5 |
| 426/160 | 2.22% by weight | 0 | 0 | 0 | 0 |
| | 1.11% by weight | (0) | (0) | 0 | 0 |
| | 0.55% by weight | (0) | (0) | 0 | 0 |
| Stress due to 72 hours leaching | | | | | |
| Time (week) | | 1 | 2 | 1 | 2 |
| Blank | | 5 | 5 | 5 | 5 |
| Parmetol DF 27 | 3.0% by weight | (0) | (0) | 0 | 0 |
| | 2.0% by weight | (0) | (0) | 0 | 0 |
| | 1.0% by weight | 1 | 1 | 0 | 0 |
| 431/043 | 2.0% by weight | 5 | 5 | 5 | 5 |
| | 1.0% by weight | 5 | 5 | 5 | 5 |
| | 0.5% by weight | 5 | 5 | 5 | 5 |
| Mar 71 | 2.0% by weight | 5 | 5 | 5 | 5 |
| | 1.0% by weight | 5 | 5 | 5 | 5 |
| | 0.5% by weight | 5 | 5 | 5 | 5 |
| 426/160 | 2.22% by weight | 1 | 1 | 0 | 0 |
| | 1.11% by weight | 1 | 1 | 0 | 0 |
| | 0.55% by weight | 1 | 1 | 0 | 0 |

Key:
00 = entire plate free from colonization
0 = zone formation (no colonization around the sample)
(0) = fungal colonization up to the sample
1 = only the sample edge is colonized
2 = the sample is colonized from the edge inwards (less than 25%)
3 = the sample surface is colonized by individual colonies (25%–75%)
4 = the sample surface is colonized extensively (75% and more, but not the entire surface)
5 = the sample surface is colonized completely (100%)

Results:

Discoloration:

Use concentrations of 2% by weight of 431/043 or Mar 71 or carbendazim did not result in any discoloration of the finished paint samples. A use concentration of 2% by weight of Mar 71 resulted in the formation of some lumps in the paint sample.

Algicidal Action:

Without stress due to leaching, 431/043 and Mar 71 (use concentration from 0.5 to 2% by weight) showed good algicidal activity, the algicidal activity of 431/043 being better than that of Mar 71 on its own. With stress due to leaching, Mar 71 and 431/043 showed little algicidal action in practice; however, 431/043 effected a reduction of growth on the surface.

Without and with stress due to leaching, carbendazim showed, at an active compound concentration of 0.2% by weight (active compound concentration based on the total composition of house paint and test substance), no algicidal action in the algae test.

Fungicidal Action:

At a use concentration of from 0.5 to 2% by weight, 431/043 showed, without stress due to leaching, a sufficiently high activity against the test germs AN and PF. Mar 71 showed no fungicidal activity in practice.

Summary:

Without stress due to leaching, 431/043 showed good algicidal and satisfactory fungicidal action against the test germs AN and PF. With stress due to leaching, the activity against algae and fungi was reduced.

EXAMPLE 2

Activity in Industrial Products

TABLE 4

Test methods and samples used

Boko test:
Test products:

| | |
|---|---|
| 431/044 A | Mar 71 |
| 431/043 | 10% by weight of carbendazim + 90% by weight of Mar 71 |

Sample 431/043 was prepared by maintaining 10% by weight of carbendazim and 90% by weight of Mar 71, based on the resulting composition, at 80–85° C. for 5 h. The mixture was subsequently filtered through a Seitz filter, giving a brown-yellow clear solution. The Boko test was carried out as described below:

In separate batches, in each case 100 ml of the water-diluted cutting fluid to be preserved were admixed with various concentrations of the preservatives to be examined. The growth control used was in each case an unpreserved sample.

Two days after the incorporation of the preservatives, the test batches were infected for the first time using 1 ml of an inoculating solution. The inoculating solution used was a suspension of the germs listed below (cultivated on nutrient media and then adapted to water-diluted cutting fluids). The inoculating solution had a titre of at least $10^7$ germs/ml.

| | | |
|---|---|---|
| Bacteria | *Escherichia coli* | ATCC 11229 |
| | *Klebsiella pneumoniae* | ATCC 4352 |
| | *Pseudomonas aeruginosa* | ATCC 15442 |
| Yeasts | *Candida albicans* | ATCC 10231 |
| | *Rhodotorula mucilaginosa* (rubra) | DSM 70403 |
| Fungi | *Fusarium oxyspocum* | ATCC 62318 |

The test batches were subsequently inoculated two times a week and plated onto agar plates two times per week, the first smear being carried out immediately prior to the new inoculation. The microbial growth on the smears was assessed after incubation at 25° C. for three days. To be on the safe side, negative smears were observed for another two days and then reassessed. The preservative effect of the individual product concentrations was assessed in a semi-quantitative method by the colonization of the individual smears using the classification from − to + to +++. Growth was differentiated according to bacteria, yeasts and moulds.

| | | |
|---|---|---|
| − | = | no colonization |
| + | = | some colonization |
| ++ | = | moderate colonization |
| +++ | = | strong colonization |

The test was usually carried out for twelve inoculation cycles or interrupted after repeated +++ growth.

Test Conditions:

The cutting fluids Shell Dromus BX or Almasol EP from Castrol or Rondocor Kompakt from Consulta were examined as 4% strength by weight emulsions in tap water from the city of Norderstedt. Inoculation was carried out using a suspension of bacteria or fungi or a mixed suspension of bacteria and fungi.

TABLE 5

Results of the Boko test according to Table 4

| | | Number of inoculation cycles passed on inoculation with: | | |
|---|---|---|---|---|
| | Use concentration | Bacteria suspension | Fungi suspension | Mixed suspension |
| Cutting fluid Shell Dromus BX, based on mineral oil | | | | |
| 431/044 A | Blank | 0 | 0 | 0 |
| | 0.15% by weight | >12 | >12 | >12 |
| | 0.10% by weight | >12 | >12 | 11 |
| | 0.05% by weight | >12 | >12 | 4 |
| 431/043 | 0.15% by weight | >12 | >12 | >12 |
| | 0.10% by weight | >12 | >12 | >12 |
| | 0.05% by weight | >12 | >12 | 0 |
| Cutting fluid Almasol EP, based on mineral oil, comprising amine | | | | |
| 431/044 A | Blank | 0 | 0 | 0 |
| | 0.15% by weight | >12 | >12 | 11 |
| | 0.10% by weight | >12 | >12 | >12 |
| | 0.05% by weight | >12 | >12 | 11 |
| 431/043 | 0.15% by weight | >12 | >12 | >12 |
| | 0.10% by weight | >12 | >12 | >12 |
| | 0.05% by weight | >12 | >12 | 11 |
| Cutting fluid Rondocor Kompakt, comprising mineral oil | | | | |
| 431/044 A | Blank | 7 | 5 | 0 |
| | 0.15% by weight | >12 | >12 | >12 |
| | 0.10% by weight | >12 | >12 | >12 |
| | 0.05% by weight | >12 | >12 | >12 |
| 431/043 | 0.15% by weight | >12 | >12 | >12 |
| | 0.10% by weight | >12 | >12 | >12 |
| | 0.05% by weight | >12 | >12 | >12 |

Results:

In cutting fluids based on mineral oil (Shell Dromus BX and Almasol EP, comprising amine), Mar 71 and the preparation of Mar 71 and carbendazim (90+10% by weight) were, in the concentration range examined, similarly effective against bacteria and fungi and against a mixed culture of bacteria and fungi. The advantages of the combination of Mar 71 and carbendazim became evident.

EXAMPLE 3

Preparations of Mar 71, Carbendazim and Other Biocides

With stirring, 800 g of Mar 71 and 100 g of carbendazim were heated at 78–80° C. for 9 hours. The slightly turbid product was filtered (presolution 437/097) and in each case admixed with 10% by weight of the following biocides (all data in per cent by weight, based on the total composition).

|  | A | B | C | D |
|---|---|---|---|---|
| Mar 71 | 10 | | | |
| Kathon 893[1] | | 10 | | |
| IPBC[2] | | | 10 | |
| Na pyrion (40% by weight) | | | | 10 |
| Presolution 437/097 | 90 | 90 | 90 | 90 |

[1]45% by weight of N-octylisothiazolone in 1,2-propylene glycol
[2]iodopropynyl butylcarbamate After filtration through a Seitz filter, all solutions were clear and light-brown.

EXAMPLE 4

Preparations Based on Mar 71 and Carbendasulf

|  | A | B | C | D | E | F |
|---|---|---|---|---|---|---|
| Mar 71 | 100 | 80 | 60 | 40 | 20 | — |
| Carbendasulf sol.* | — | 20 | 40 | 60 | 80 | 100 |

*10.5% by weight of carbendasulf in 1,2-propylene glycol

After mixing the starting materials, clear, colourless to yellowish solutions are obtained.

EXAMPLE 5

Activity of Compositions of Mar 71 and Carbendazim

Preparations:

| G 5620 | 1% by weight carbendazim + 99% by weight Mar 71 |
| G 5621 | 2% by weight carbendazim + 98% by weight Mar 71 |
| G 5622 | 5% by weight carbendazim + 95% by weight Mar 71 |
| G 5623 | 10% by weight carbendazim + 90% by weight Mar 71 |
| G 5624 | Mar 71 |

Solutions of in each case 2% strength by weight in fully deionized water were examined against selected bacteria and/or yeasts and/or fungi and/or algae using the serial dilution test according to DGHM [German Society for Hygiene and Microbiology].

MIC values of the aqueous 2% by weight strength solutions:

|  | PS | EC | KP | CA | RM | FO | PF | AN | AL | CF |
|---|---|---|---|---|---|---|---|---|---|---|
| G 5620 | 6.25 | 6.25 | 6.25 | >6.25 | 1.56 | 0.78 | 0.78 | 1.56 | 6.25 | 0.78 |
| G 5621 | 6.25 | 6.25 | 6.25 | >6.25 | 3.12 | 0.19 | 0.19 | 0.39 | 6.25 | 0.39 |
| G 5622 | 6.25 | 6.25 | 6.25 | >6.25 | 1.56 | 0.09 | 0.09 | 0.39 | 6.25 | 0.39 |
| G 5623 | 6.25 | 6.25 | 6.25 | >6.25 | 6.25 | 0.09 | 0.09 | 0.19 | 6.25 | 0.39 |
| G 5624 | 6.25 | 6.25 | 3.12 | >6.25 | 3.12 | 1.56 | 1.56 | 6.25 | 6.25 | 0.39 |

Key to Microorganisms:

| Bacteria: | PS | = | *Pseudomonas aeruginosa* |
| | EC | = | *E. coli* |
| | KP | = | *Klebs. pneumoniae* |
| Yeasts: | CA | = | *Cand. albicans* |
| | RM | = | *Rhodotorula mucilaginosa* |
| Fungi: | FO | = | *Fusarium oxysporum* |
| | AN | = | *Asperg. niger* |
| | PF | = | *Penicillium funiculosum* |
| | AL | = | *Alternaria alternata* |
| Algae: | CF | = | *Chlorella fusca* |

The emboldened MIC values denote preparations which were more effective than Mar 71. In particular in the case of some yeasts and fungi, the preparations according to the invention were considerably more effective than Mar 71 on its own.

What is claimed is:

1. A stable microbicidal composition, consisting essentially of 3,3'-methylenebis-(5 methyloxa-zolidine) and derivates of 1H-benzimidazol-2-ylcarbamic acid selected from the group consisting of methyl 1H-benzimdazol-2-ylcarbamate or its salts, and methyl 1-(butylcarbamoyl) benzimidazol-2-ylcarbamate and optionally additives, auxiliaries, and microbicidally active compounds selected from the group consisting of N-formals and O-formals.

2. The composition according to claim 1, wherein the composition has a pH of up to 12.

3. The composition according to claim 2, wherein the composition has a pH of up to 10.

4. The composition according to claim 1, wherein additives, auxiliaries, and microbicidally active compounds selected from the group consisting of N-formals and O-formals are present.

5. The composition according to claim 1, wherein the composition is in aqueous and/or organic phases.

6. The composition according to claim 1, wherein the composition is present in the form of a liquid, liquid-viscous, or paste.

7. The composition according to claim 1, wherein the composition is present as a concentrate.

8. The composition according to claim 1, wherein the composition is present in the form of a ready-to-use solution.

9. The composition according to claim 1, wherein the content of carbamic acid derivative is greater than 5% by weight.

10. The composition according to claim 9, wherein the content of carbamic acid derivative is greater than 10% by weight.

11. The composition according to claim 1, wherein the content of methylenebisoxazolildine derivative is not greater than 99% by weight.

12. The composition according to claim 11, wherein the content of methylenebisoxazolildine derivative is not greater than 90% by weight.

13. Method of adding a composition according to claim 1, an industrial product selected from the group consisting of crop protection compositions, compositions for the treatment of seed, industrial preservatives having microbicidal activity, cutting fluid additives, fuel additives, disinfectants, compositions for treating plant pruning wounds, film preservatives for external and internal applications, and wood protection compositions, the method comprising adding the composition in concentrations of greater than 0.01% by weight based on the weight of the industrial product.

14. The method according to claim 13, wherein the composition is added in concentrations of greater than 0.10% by weight based on the weight of the industrial product.

15. The method according to claim 13, wherein the components of the composition are incorporated into the industrial product separately at different times.

16. Method of increasing the solubility of derivatives of 1H-benzimidazol-2-ylcarbamic acid selected from the group consisting of methyl 1H-benzimdatol-2-ylcarbamate or its salts and methyl 1-(butylcarbamoyl) benzimidazol in a liquid preparation, consisting essentially of adding to said liquid preparation an effective amount of 3,3'-methylenebis (5 methylox-azolidine) and optionally additives, auxiliaries, and microbicidally active compounds selected from the group consisting of N-formals and O-formals.

17. The method according to claim 16, wherein additives, auxiliaries, and microbicidally active compounds selected from the group consisting of N-formals and O-formals are present.

18. The method according to claim 16, wherein the liquid preparation is in aqueous and/or organic liquid phases.

19. The method according to claim 16, wherein the liquid preparation has a pH of up to 12.

20. The method according to claim 19, wherein the liquid preparation has a pH of up to 10.

21. The method according to claim 16, wherein the content of carbamic acid derivative in the liquid preparation is greater than 1% by weight.

22. The method according to claim 21, wherein the content of carbamic acid derivative in the liquid preparation is greater than 10%.

23. The method according to claim 16, wherein the content of methylenebisoxazolildine derivative in the liquid preparation is not greater than 99% by weight.

24. The method according to claim 23, wherein the content of methylenebisoxazolildine derivative in the liquid preparation is not greater than 90% by weight.

25. The method according to claim 16, wherein the liquid preparation is present in the form of a concentrate or a ready-to-use solution.

* * * * *